United States Patent [19]

Nash

[11] Patent Number: 4,615,472

[45] Date of Patent: Oct. 7, 1986

[54] CATHETER PLACEMENT DEVICE

[75] Inventor: John Nash, Downingtown, Pa.

[73] Assignee: Intravascular Surgical Instruments, Inc., Downingtown, Pa.

[21] Appl. No.: 746,414

[22] Filed: Jun. 19, 1985

[51] Int. Cl.⁴ .......................................... B65H 20/00
[52] U.S. Cl. ................... 226/127; 128/657; 604/159; 604/178; 604/280
[58] Field of Search ............... 128/657; 604/159, 163, 604/164, 165, 171, 172, 178, 280; 226/127

[56] References Cited

U.S. PATENT DOCUMENTS

| | | | |
|---|---|---|---|
| 973,345 | 10/1910 | Dalton . | |
| 2,009,825 | 7/1935 | Wappler | 604/171 |
| 3,298,666 | 1/1967 | Prange | 226/127 |
| 3,472,232 | 10/1969 | Earl | 604/165 |
| 3,515,137 | 6/1970 | Santomieri | 604/165 |
| 3,521,620 | 7/1970 | Cook | 128/772 |
| 3,537,451 | 11/1970 | Beck et al. | 604/165 |
| 3,547,103 | 12/1970 | Cook | 128/2.05 |
| 3,625,200 | 12/1971 | Muller | 128/2.05 R |
| 3,682,173 | 8/1972 | Center | 604/159 |
| 3,766,915 | 10/1973 | Rychlik | 604/163 |
| 3,773,034 | 11/1973 | Burns et al. | 128/2 M |
| 3,908,487 | 9/1975 | Plaw | 81/59.1 |
| 3,941,119 | 3/1976 | Corrales | 128/657 |
| 4,020,829 | 5/1977 | Willson et al. | 128/2 M |
| 4,177,809 | 12/1979 | Moorehead | 604/165 |
| 4,287,891 | 9/1981 | Peters | 604/174 |
| 4,326,520 | 4/1982 | Alley | 604/159 |

Primary Examiner—Edward M. Coven
Assistant Examiner—Ruth S. Smith
Attorney, Agent, or Firm—Caesar, Rivise, Bernstein & Cohen, Ltd.

[57] ABSTRACT

A slip gripping device for use with an elongated cylindrical member to selectively move that member to any desired longitudinal or rotational position. The device comprises a collet-like member including a plurality of fingers, each of which includes a gripping element at the free end thereof. The collet member is arranged to be grasped and squeezed whereupon its fingers are flexed so that the gripping elements engage the surface of the cylindrical member so that rotary motion imparted to the slip grip device causes the concomitant rotation of the flexible member so that any longitudinal movement of the device causes concomitant longitudinal movement of the member. Release of the collet-like member enables the slip grip device to be slid and rotated with respect to the cylindrial member for positioning anywhere there along.

18 Claims, 6 Drawing Figures

CATHETER PLACEMENT DEVICE

BACKGROUND OF THE INVENTION

This invention relates generally to medical devices and more particularly to devices for use with intralumen catheters or guide wires therefore.

Many medical diagnostic and treatment techniques involve the use of a catheter for introduction into a passageway, e.g., a blood vessel, in the patients body. In order to locate the catheter in a small remotely located distal branch vessel the catheter itself or a guide wire for a catheter has to be inserted into the body and guided through various small compound curves and branches. In the case of a guide wire, once the guide wire is in place the catheter is then slid down the guide wire to the desired location, and the guide wire removed or left in place, as the case may be.

One prior art technique for effectuating the placement of a catheter or guide wire (hereinafter referred to as catheter/guide wire) at a remotely located position within a blood vessel involves the use of a steerable catheter/guide wire having a curved or curvable distal end or tip. That device is then fed from its percutaneous introduction site, e.g., the femoral artery, down the artery or vein while its movement is observed by means of a fluoroscope or other suitable scanning device. When the catheter/guide wire reaches a branch the catheter/guide wire is manipulated by applying rotary torque to it. Such torque is applied at a point proximally from the percutaneous introduction site and results in the rotation of the catheter/guide wire about its longitudinal axis. The rotary torque is applied until the catheter/guide wire is rotated to the position at which its curved distal end is pointed in the desired vascular branch direction. The catheter/guide wire can then be fed further into (distally) the vessel. This procedure continues and is repeated until the distal end of the catheter/guide wire is located at the desired intravascular location.

Examples of prior art steerable catheters/guide wires are shown in U.S. Pat. Nos. 3,521,620 (Cook), 3,547,103 (Cook), and 4,020,829 (Wilson et al.).

Some prior art steerable catheters/guide wires make use of a controllably curvable tip. For example, one type of steerable tip catheter involves the use of plural control wires extending the length of the catheter from its tip to some proximally located steering device. The steering device operates the various control wires to bend the tip in the desired direction. Another type of steerable tip catheter involves the use of singular fluid pressure means in combination with restraining means to bend the catheter from a straight orientation to a predetermined curved orientation extending in a predetermined direction. The use of plural fluid pressure means in lieu of a single fluid pressure means enables the tip to be bent into a curved orientation extending in any one of several directions. Examples of such steerable catheters are shown in U.S. Pat. Nos. 3,625,200 (Muller) and 3,773,034 (Burns et al.).

While the foregoing prior art catheters appear generally suitable for their intended purposes they leave much to be desired from the standpoint of simplicity of construction and use. Moreover the steering means for such catheters, by being built into the catheter thus prevents its use with other types of catheters and/or guide wires. Thus, the need exists for a device which can be used with conventional catheters/guide wires or other elongated flexible shaft instruments to effect the selective gripping and longitudinal and/or rotational movement thereof.

With regard to the need for effecting the selective rotation of a shaft, it will, of course, be appreciated by those skilled in the art that various chuck-type devices have been disclosed in the literature for gripping the periphery of a rigid shaft to rotate the shaft about its longitudinal axis. For example U.S. Pat. No. 3,908,487 (Plaw) discloses a screwdriver having a handle including a plurality of rollers disposed about the shaft of the screwdriver and which are arranged to selectively roll along a lobed sleeve to move the rollers into tight engagement with the shaft so that the shaft will rotate when the handle of the screwdriver is rotated. U.S. Pat. No. 973,345 (Dalton) discloses a drill chuck which is constructed and which operates in a similar manner to the screwdriver of the Plaw patent.

While the foregoing prior art chuck type devices are generally suitable for their intended purposes, i.e., to effect rotation of a rigid shaft, they do not enable the positioning of the same along the shaft to any desired position. Moreover such devices do not appear suitable for use with a flexible shaft medical instrument of small outside diameter, such as a catheter/guide wire, to effect the rotation thereof from a point outside the body.

OBJECT OF THE INVENTION

Accordingly, it is the general object of the instant invention to provide a device which overcomes the disadvantages of the prior art.

It is a further object of the instant invention to provide a device for effecting the selective and controlled rotation and/or longitudinal positioning of an elongated shaft.

It is still a further object of the instant invention to provide a steering device which is arranged for effecting the selective and controlled rotation and/or longitudinal positioning of an elongated flexible shaft, such as a catheter/guide wire therefore, and which device can be readily moved with respect to said catheter/guide wire.

It is still a further object of the instant invention to provide a steering device for effecting the placement of a catheter/guide wire or any other flexible elongated shaft and which is simple in construction and low in cost.

It is still a further object of the instant invention to provide a steering device for effecting the precise controlled placement of a catheter/guide wire or any other flexible elongated shaft and yet which is simple to use.

SUMMARY OF THE INVENTION

These and other objects of the instant invention are achieved by providing a device for use within an elongated cylindrical member having a longitudinal axis. The device is arranged to be slideable to a predetermined longitudinal position on the member and arranged to be actuated from the first state to a second state to enable the controlled rotation or linear movement of the member with respect to that axis. The device comprises a plurality of first gripping elements disposed about a periphery of a portion of the cylindrical member and actuatable means coupled to the elements. The actuatable means is arranged to be actuated from the first state to the second state. When the actuatable means is in the first state the gripping elements are spaced slightly from the periphery of the portion of the cylindrical member so that the device can be readily slid along the member. When the actuatable means is in the second state selected ones of the gripping elements frictionally engage the surface of the elongated cylindrical member, whereupon rotary motion about the longitudinal axis or linear motion along that axis and which is imparted to the device causes concomitant movement of the elongated member.

DESCRIPTION OF THE DRAWINGS

Other objects and many of the attendant advantages of the instant invention will be readily appreciated as the same becomes better understood by reference to the following detailed description when considered in connection with the accompanying drawings wherein.

DETAILED DESCRIPTION OF THE PREFERRED EMBODIMENTS

Figure 1:
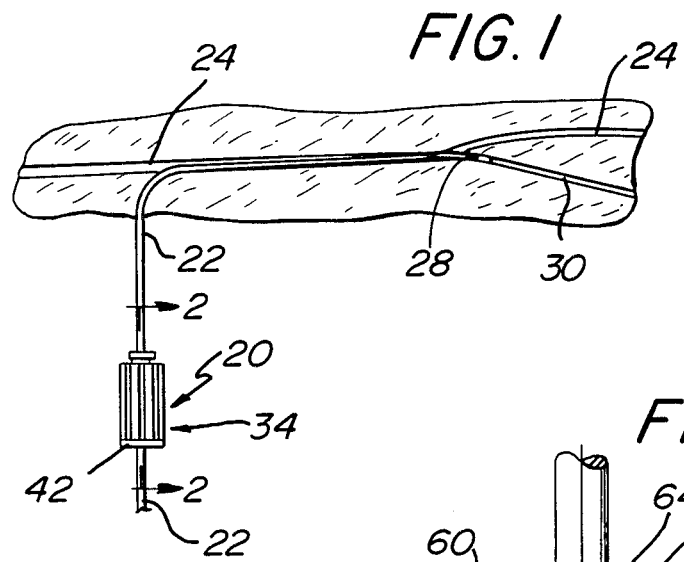
FIG. 1 a schematic diagram showing the device of the instant invention used with a catheter/guide wire for placement of the catheter/guide wire at a desired intravascular position.

Referring now in greater detail to the various figures of the drawing wherein like reference characters refer to like parts, there is shown at 20 in FIG. 1 a device for positioning an elongated shaftlike member in a desired rotational orientation and/or at a desired longitudinal position. While the device 20 is shown and described herein for particular use with a catheter and/or a guide wire, it must be pointed out that the device can be used with any shaft, flexible or otherwise, which for its placement and/or use, needs to be positioned at a desired longitudinal position with respect to a body and/or rotated about its longitudinal axis to a desired orientation.

Owing to the simplicity of its structure and its operational features, the device 20 has particular utility in medical applications and more particularly for use in the placement of intravascular catheters/guide wires or other flexible shaft instruments within a lumen in the body. Thus, in FIG. 1, the device 20 is shown in a typical application for positioning a conventional flexible shaft catheter 22 at a desired distal position within an artery 24 of a person. In the interest of drawing simplicity the catheter/guide wire 22 is shown as being tubular in cross section, but none of its interior features shown.

In order to position the catheter/guide wire at the desired distal position. The catheter/guide wire must be slid down the artery from its subcutaneous point of introduction (not shown) to the desired distal location. As will be described in considerable detail later, the device 20 is used to effect such positioning. To that end the device is placed on the catheter/guide wire spaced proximally from the subcutaneous introduction point. The device is then squeezed (manually or by some gripping means) to cause it to grip the surface of the catheter/guide wire. Force is then applied to the device 20 in the distal direction along the longitudinal axis 26 of the catheter/guide wire. This action causes the catheter/guide wire to move down the artery. The device is then released (unsqueezed) to free it from the catheter/guide wire so that it can be slid back along the axis thereof in the proximal direction for the next advancement or a rotation step (to be described). In order to facilitate the navigation of the various branches of the artery to reach the desired position, the catheter/guide wire 22 preferably includes a slightly curved distal end or tip 28. Thus, each time that a branch artery 30 (FIG. 1) is reached the catheter/guide wire 22 can be rotated about its longitudinal axis to a precise directional orientation so that its tip 28 is aligned with and can readily enter the branch artery. The device 20 effectuates such rotational placement of the catheter/guide wire. This action is also accomplished by squeezing the device 20 to cause it to grip the catheter/guide wire. The device is then rotated about its longitudinal axis (which is also the longitudinal axis of the catheter/guide wire) to apply rotary torque thereto and thus cause the catheter/guide wire to rotate about its axis so that its curved tip is in the desired orientation.

Figure 3:
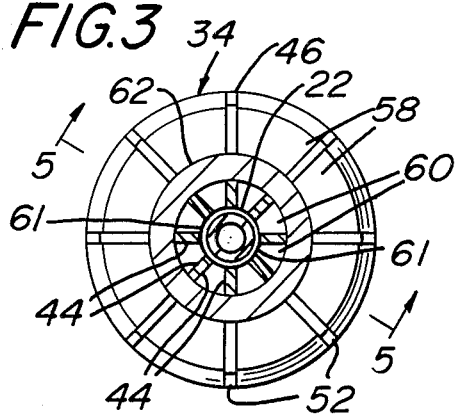
FIG. 3 is an enlarged sectional view taken along line 3—3 of FIG. 2.
Figure 4:
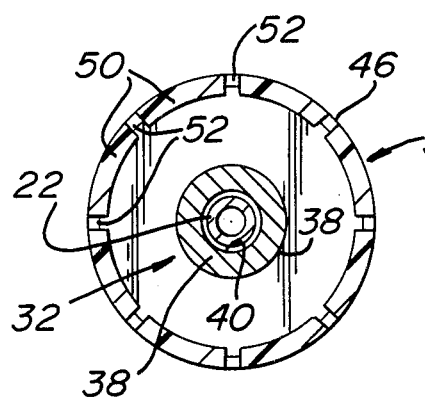
FIG. 4 is an enlarged sectional view taken along line 4—4 of FIG. 2.
Figure 2:
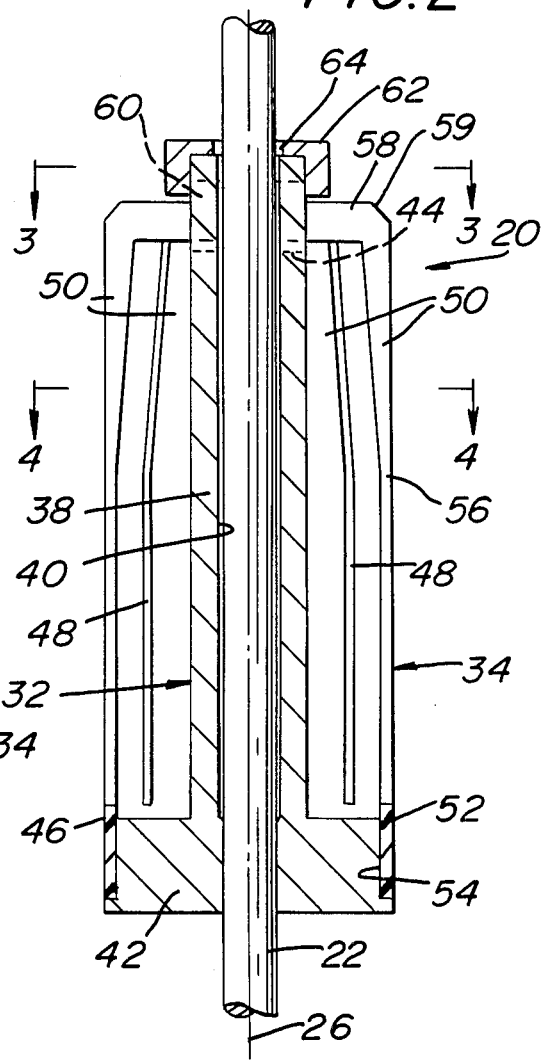
FIG. 2 is an enlarged sectional view taken along line 2—2 of FIG. 1.

As can be seen in FIG. 2, the device 20 basically comprises a sleeve element 32, through which the catheter/guide wire passes, and a collet-like member 34 having plural gripping means (to be described later) and actuatable means (also to be described later) therefore. The sleeve 32 is in the form of a bushing, formed of a lightweight, yet strong material, e.g., aluminum, and having an elongated tubular body section 38 including a central passageway 40 extending therethrough and through which the catheter/guide wire 22 passes. Thus, the longitudinally extending axis 26 of the catheter/guide wire also serves as the central longitudinal axis of the device 20. The tubular body section 38 terminates at one end (the lower end in FIG. 2) in a annularly extending peripheral flange 42 and at the other end in a plurality of radially extending slots 44 (FIGS. 2 and 3). The slots 44 extend through the sidewall of the body section 38 in a direction parallel to the longitudinal axis 26 of the device and are open at the free end of the section 38.

As shown clearly in FIG. 3, the inside diameter of the passageway 40 is just slightly greater than the outside diameter of the catheter/guide wire 22 to enable the device 20 to be freely slid therealong.

The collet-like member 34 comprises a tubular body section 46 having plural longitudinally extending slots 48 located at equadistantly placed positions about the periphery of the tubular body. The slots form therebetween a plurality of longitudinally extending finger-like elements 50. These elements form the actuatable means for the device 20. Each element 50 extends generally parallel to the axis 26 of the device from an unslotted end 52 of body section 46. The unslotted end of section 46 is mounted within an annular ledge or recess 54 in the outer periphery of the flange 42.

As can be seen clearly in FIG. 2 the thickness of each of the finger-like elements 50 increases from a point 56 adjacent its mid-point to the free end 59 thereof. The free end of each of the finger-like elements is in the form of an inwardly radially extending wedge shaped flange 58. The free end of each flange 58 is in the form of a longitudinally projecting shoe like extension 60. Each extension forms a respective gripping element making up the heretofore mentioned gripping means. Thus, the inner surface 61 of each gripping element 60 is a concave cylindrical surface corresponding to the circular periphery of the catheter 22.

The collet-like member 34, composed of the gripping elements 60, fingers 50 and section 46, is formed as an integral unit of a strong, tough, yet flexible material, e.g., a plastic, to enable the fingers 50 to be readily flexed (in a manner to be described hereinafter) to effect the gripping action of the elements 60 about the periphery of the catheter/guide wire passing therethrough.

As can be seen in FIG. 2 a retaining cap 62, also formed of a lightweight and strong material, such as aluminum, is fixedly mounted on the slotted end of the sleeves body section 38. The cap 62 includes a central passageway 64 in communication with the passageway 40 in the section 38 and through which the catheter/guide wire 22 passes.

Figure 5:
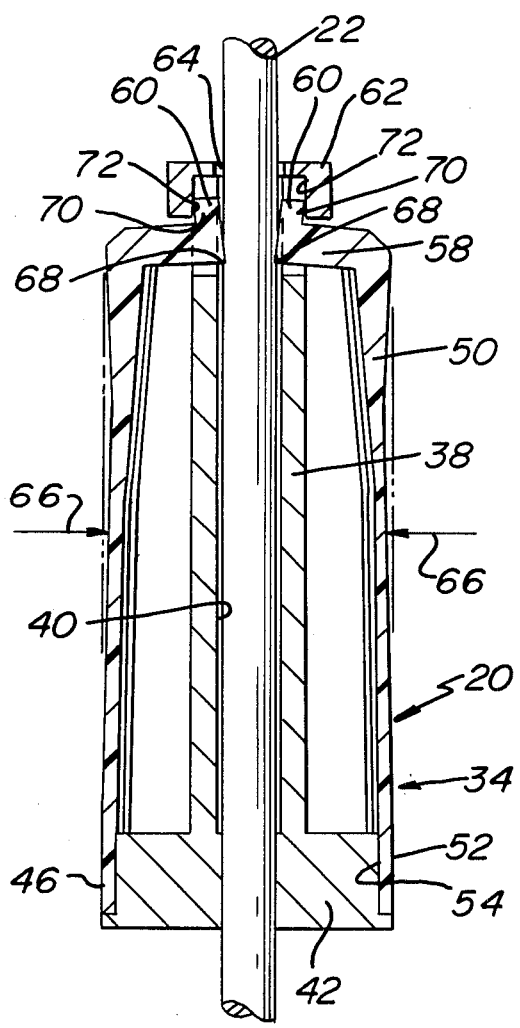
FIG. 5 is an enlarged sectional view like that shown in FIG. 2 but showing the device in its gripping mode or state.

Operation of the device 20 can best be understood by reference to FIGS. 2 and 5. In particular in FIG. 2 the device 20 is shown in its relaxes or non-gripping state. In that state the device 20 can be freely slid along the catheter/guide wire to any desired longitudinal position. Moreover the device can be rotated with respect to the catheter/guide wire about the axis of the catheter/guide wire.

In order to move the catheter/guide wire down the artery and/or to rotate it about its longitudinal axis within the artery, the collet member 36 is grasped and squeezed radially inward. Such action can be effected either manually by the physician or by any suitable mechanical means (not shown). In either case the application of an inward radial load to the fingers of the collet (such a load being depicted symbolically by the arrow 66 in FIG. 5) causes the fingers 50 to flex slightly from their phantom line position shown in FIG. 5 to the solid line position shown therein. This flexure of the fingers causes the proximally located inner corner 68 of each of the gripping elements 60 to pivot slightly toward the axis 26 and into contact with the periphery of the catheter/guide wire while at the same time the distally located outer corner 70 of each of th gripping elements 60 bear against the inner surface 72 of the cap 62. The combined effect of that action is that the portions 68 of elements 60 engage the periphery of the catheter/guide wire 22 in sufficiently tight frictional engagement that linear or rotary movement of the device 20 will cause the catheter/guide wire to move concomitantly therewith. Thus, all that is required of the physician to rotate the catheter/guide wire 22 to any desired orientation is to grasp and squeeze the device 20 and then while squeezing the device to rotate it about its axis 26 to the desired angular orientation. Once the catheter/guide wire is in that angular orientation it can be advanced by merely applying a load, e.g., pushing, on the device 20 in a distal direction along its axis 26 while at the same time squeezing its collet member. After the catheter/guide wire 22 has been so moved the physician merely releases the squeezing load on the device so that its fingers 50 automatically flex back to their unflexed state, that is the phantom line position in FIG. 5 (the full line position in FIG. 2) whereupon the device 20 can be freely slid and/or rotated with respect to the catheter/guide wire to position the device at any desired position thereon. Removal of the catheter/guide wire is accomplished by merely grasping and squeezing the device, while pulling on it in the proximal direction.

Figure 6:
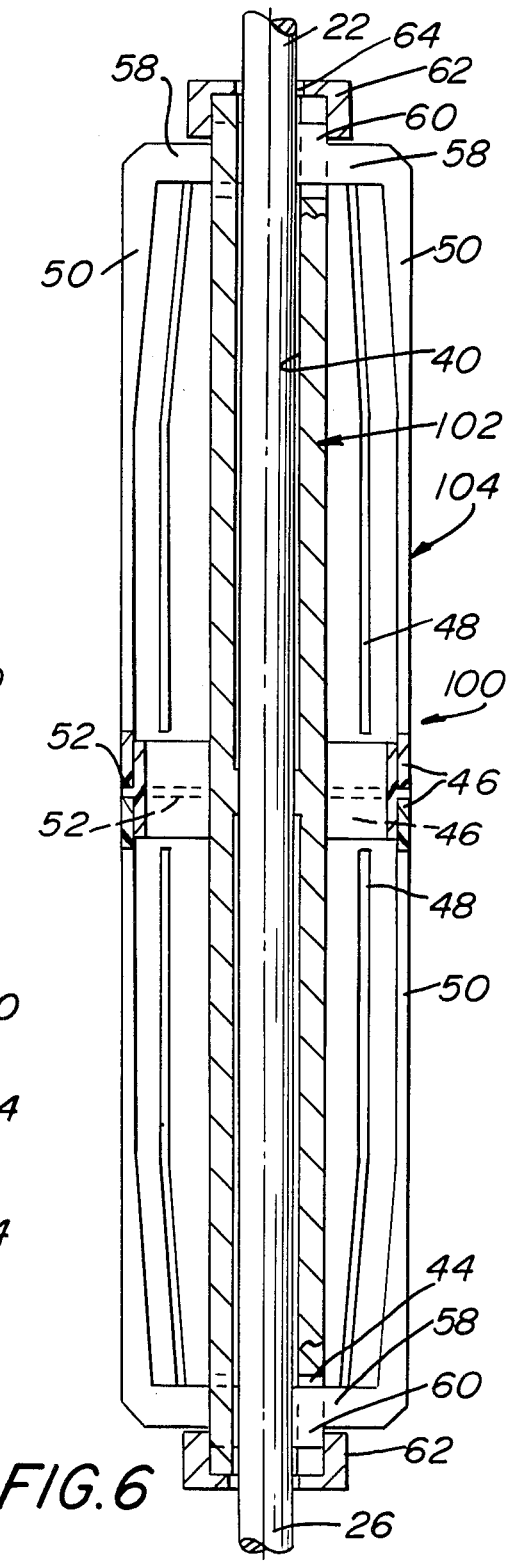
FIG. 6 is an enlarged sectional view, similar to that of FIG. 2 but showing an alternative embodiment of the device of the instant invention.

In FIG. 6 there is shown an alternative embodiment of a catheter steering device constructed in accordance with this invention. That alternative device is denoted by the reference numeral 100 and basically comprises a double-ended version of the device 20 described heretofore. Thus, as can be seen in FIG. 6 the sleeve means is formed of an elongated tubular body section 102, constructed like tubular body section 38 described heretofore but without the use of any flange. Instead each end of the sleeve body 102 is constructed identically to the slotted end of the sleeve device 20.

In the interest of brevity the common structural features of the sleeve body 102 of device 100 and that of sleeve body 38 of device 20 are given the same reference numerals. To that end as can be seen each end of the sleeve body 102 includes plural slots 44 which are each adapted to receive a respective gripping element 60 of the device's collet-like member 104 (to be described hereinafter). A respective cap 62 is mounted on each slotted end of the sleeve body 102.

As can be seen the collet means 104 basically consists of two of the collet-type grasping members 34 described heretofore but disposed back to back with each other, that is abutting at their respective tubular end portions 52. The two members are secured to each other via the use of an adhesively secured, internal bridging sleeve 106. Accordingly, the common structural features of the grasping member 104 of device 100 are given the same reference numerals as the grasping member 34 of device 20.

As will be appreciated by those skilled in the art the operation of device 100 is the same as that of device 20 save for the fact that the application of a radial squeezing load to its midsection results in greater gripping engagement with the catheter/guide wire owing to the fact that the gripping elements 60 of embodiment 100 engage the catheter/guide wire in two areas, as opposed to the single area of grip which results from the use of device 20.

It should be pointed out at this juncture that while the sleeve and cap elements of the devices described heretofore are stated as being formed of aluminum and the collet-like grasping member being formed of plastic, such materials are not exclusive and any other suitable materials can be used for any of the components herein.

As will be appreciated from the foregoing the device of the instant invention is simple in construction and can thus be manufactured at low cost. Moreover, the device has wide applicability for use with any type catheter/guide wire or other elongated flexible element which has to be precisely positioned within the body of a patient. In fact, it should be pointed out that the device of the instant invention could be used to longitudinally and rotationally position any type of shaft-like element whether flexible or rigid.

Without further elaboration, the foregoing will so fully illustrate my invention that others may, by applying current or future knowledge, readily adopt the same for use under various conditions of service.

I claim:

1. A device for effecting the positioning of an elongated cylindrical member having a longitudinal axis, said device when in a first state being slideable to a predetermined longitudinal position on said member and arranged to be actuated from said first state to a second state to effect the controlled rotation and/or linear movement of said member with respect to said axis, said device comprising a sleeve having a longitudinal passage therethrough, and which is open at each end for receiving and passing said cylindrical member freely therethrough, said sleeve having a plurality of longitudinal extending slots disposed about the periphery of said sleeve, and actuating means including portions fixedly positioned and extending longitudinally along said sleeve and further including plural gripping elements adapted to pass through said slots in said sleeve for selectively gripping said cylindrical member, said plural gripping elements disposed adjacent said slots, said actuating means being arranged to be actuated from said first state to said second state, said gripping elements, when said actuating means is in said first state, being spaced slightly from the periphery of said cylindrical member, whereupon said device can be readily slid along said cylindrical member to said predetermined location, and said gripping elements, when said actuating means is in said second state, extending through said slots and frictionally engaging the surface of said cylindrical member about the periphery thereof, whereupon rotary motion of said device about said axis or linear motion of said device along said axis causes concomitant movement of said cylindrical member.

2. The device of claim 1 wherein said portions comprise a plurality of moveable fingers, said gripping elements being mounted on said fingers adjacent said slots.

3. The device of claim 2 wherein said fingers are mounted on said sleeve and include portions extending along the outside of said sleeve parallel to said longitudinal passage through said sleeve to serve as a grasping surface.

4. The device of claim 3 wherein said gripping elements are positioned at the ends of said fingers opposite the ends mounted on said sleeve.

5. The device of claim 4 wherein said fingers and gripping elements are formed as an integral unit.

6. The device of claim 5 wherein said fingers and said gripping elements are formed of a plastic material.

7. The device of claim 2, wherein said gripping elements are comprised of:
radially extending wedge-shaped flanges extending from said fingers inwardly toward said slots in said sleeve means; and
longitudinally projecting shoe extensions at the end of said wedge-shaped flanges opposite said fingers.

8. The device of claim 1 wherein said actuating means comprises two sets of plural moveable fingers, a first set of fingers including portions extending along the outside of said sleeve parallel to said longitudinal passage through said sleeve in one direction and a second set of fingers including portions extending along the outside of said sleeve parallel to said longitudinal passage in the opposite direction, said first and second sets of fingers being mounted on said sleeve between the opposite extending ends thereof, and said gripping elements being mounted on the opposite extending ends of said fingers.

9. The device of claim 8 wherein said fingers and said gripping elements are formed as an integral unit.

10. The device of claim 1 further comprising cap means surrounding said slots in said sleeve for retaining said gripping elements within said slots.

11. An apparatus for gripping an elongated cylindrical member having a longitudinal axis, said apparatus comprising:
sleeve means having a longitudinal passageway therethrough, said passageway being open at each end, for receiving and passing said cylindrical member longitudinally therethrough, said sleeve means having a plurality of slots around the circumference thereof; and
actuating means including portions fixedly positioned longitudinally on said sleeve means and extending along the length of said sleeve means, said actuating means further including plural gripping elements aligned with and adapted to pass through said slots in said sleeve means for gripping said cylindrical member passing through said passageway when said actuating means is compressed.

12. An apparatus as claimed in claim 11, further comprising:
cap means surrounding said slots in said sleeve means for retaining said gripping elements within said slots.

13. An apparatus as claimed in claim 11, wherein said portions comprise
a plurality of finger elements spaced from each other and extending from said body section along the outside of said sleeve means, said finger elements being substantially parallel to the longitudinal passageway of said sleeve means; and wherein
one gripping element is mounted on each finger element and spaced from said body section, each gripping element extending radially inwardly toward said sleeve means through one of said slots in said sleeve means; and wherein said actuating means further comprises a body section mounted on said sleeve means.

14. An apparatus as claimed in claim 13, wherein said gripping elements are comprised of:
radially extending wedge-shaped flanges extending from said finger elements inwardly toward said slots in said sleeve means; and
longitudinally projecting shoe extensions at the end of said wedge-shaped flanges opposite said finger elements.

15. An apparatus as claimed in claim 11, wherein:
said sleeve means has a plurality of slots around the circumference thereof at at least two spaced positions along the length thereof; and
a plurality of said actuating means are mounted on said sleeve means between said spaced slots, each of said actuating means extending along the length of said sleeve means toward opposite ends thereof from a position between said spaced slots, and each of said actuating means being aligned with and adapted to pass through said slots in said sleeve means at one of said spaced positions for gripping said cylindrical member passing through said sleeve means when said actuating means are compressed.

16. An apparatus as claimed in claim 15, further comprising:
a plurality of cap means surrounding said spaced slots in said sleeve means for retaining said gripping elements within said slots.

17. An apparatus as claimed in claim 15, wherein each of said portions comprise
a plurality of finger elements spaced from each other and extending from said body section along and substantially parallel to the longitudinal passageway through said sleeve means on the outside of said sleeve means; and wherein
one gripping element is mounted on each finger element and spaced from said body section, each gripping element extending radially inwardly toward said sleeve means through one of said slots in said sleeve means; and wherein each of said actuating means further comprises a body section mounted on said sleeve means.

18. An apparatus as claimed in claim 17, wherein said gripping elements are comprised of:
radially extending wedge-shaped flanges extending from said finger elements inwardly toward said slots in said sleeve means; and
longitudinally projecting shoe extensions at the end of said wedge-shaped flanges opposite said finger elements.

* * * * *